US012633388B2

(12) United States Patent　　(10) Patent No.:　US 12,633,388 B2
Jaskulski et al.　　(45) Date of Patent:　May 19, 2026

(54) SYSTEM AND METHOD FOR SELECTING OPTICAL ELEMENTS FOR VISION CORRECTION OR TREATMENT

(71) Applicant: The Trustees of Indiana University, Bloomington, IN (US)

(72) Inventors: Mateusz Tomasz Jaskulski, Bloomington, IN (US); Peter Kollbaum, Bloomington, IN (US)

(73) Assignee: The Trustees of Indiana University, Bloomington, IN (US)

( * ) Notice: Subject to any disclaimer, the term of this patent is extended or adjusted under 35 U.S.C. 154(b) by 333 days.

(21) Appl. No.: 18/397,419

(22) Filed: Dec. 27, 2023

(65) Prior Publication Data

US 2024/0221881 A1　　Jul. 4, 2024

Related U.S. Application Data

(60) Provisional application No. 63/477,493, filed on Dec. 28, 2022.

(51) Int. Cl.
*G16H 20/10* (2018.01)
*A61B 3/00* (2006.01)
*A61B 3/036* (2006.01)
*G16H 10/60* (2018.01)
*G16H 20/00* (2018.01)

(52) U.S. Cl.
CPC ........... *G16H 20/00* (2018.01); *A61B 3/0025* (2013.01); *A61B 3/036* (2013.01); *G16H 10/60* (2018.01)

(58) Field of Classification Search
CPC ...... G16H 10/60; G16H 20/00; A61B 3/0025; A61B 3/036; A61B 3/00; A61B 3/0016; A61B 3/0033; A61B 3/028; A61B 3/10; A61B 3/36; A61B 3/04
USPC ..... 351/205, 206, 227, 230, 159.73, 159.74, 351/159.75, 159.76, 159.7, 7, 159.78, 246
See application file for complete search history.

(56) References Cited

U.S. PATENT DOCUMENTS

| | | | | |
|---|---|---|---|---|
| 9,885,887 | B2 * | 2/2018 | Gardner | G02C 13/003 |
| 9,925,038 | B2 * | 3/2018 | Yoon | G02C 7/027 |
| 10,018,854 | B2 * | 7/2018 | Crespo | G06N 5/025 |
| 2002/0196412 | A1 * | 12/2002 | Abitbol | G02C 7/02 |
| | | | | 351/219 |
| 2013/0231941 | A1 * | 9/2013 | Pham | G16H 70/60 |
| | | | | 705/2 |
| 2014/0109026 | A1 * | 4/2014 | Wang | G03F 1/36 |
| | | | | 716/53 |
| 2014/0125954 | A1 * | 5/2014 | Kingston | G02C 7/028 |
| | | | | 351/246 |
| 2016/0313576 | A1 * | 10/2016 | Gardner | G02C 13/003 |
| 2017/0265738 | A1 * | 9/2017 | Keita | A61B 3/1015 |
| 2017/0371178 | A1 * | 12/2017 | Crespo | G02C 7/024 |
| 2018/0092525 | A1 * | 4/2018 | Lai | A61B 3/0285 |

(Continued)

*Primary Examiner* — William R Alexander

(74) *Attorney, Agent, or Firm* — Faegre Drinker Biddle & Reath LLP

(57) ABSTRACT

Computer-implemented tools to assist a clinician in selecting a lens or other optical element for an optimal patient treatment, such as correction, based on both the optical properties of the patient's eye and certain patient-specific use-case information such as viewing behavior or viewing preferences, or to effect treatment such as to control myopia progression. Clinicians, eye care professionals and others can provide patient-optimized lens fitting or design by use of the tools.

16 Claims, 9 Drawing Sheets

(56)     References Cited

U.S. PATENT DOCUMENTS

| 2023/0148857 A1* | 5/2023 | Neal | G16H 40/67 |
| | | | 351/219 |
| 2023/0218160 A1* | 7/2023 | Lai | A61B 3/0083 |
| | | | 351/233 |
| 2023/0284902 A1* | 9/2023 | Miseikis | G06V 10/82 |
| 2024/0005375 A1* | 1/2024 | Struck | G06Q 30/0621 |
| 2024/0049961 A1* | 2/2024 | Sela | A61B 3/022 |

* cited by examiner

SYSTEM AND METHOD FOR SELECTING OPTICAL ELEMENTS FOR VISION CORRECTION OR TREATMENT

REFERENCE TO RELATED APPLICATION

This application claims the benefit of U.S. Provisional Application No. 63/477,493 filed on Dec. 28, 2022 and entitled System and Method for Selecting Optical Elements for Vision Correction or Treatment, the disclosure of which is incorporated herein by reference in its entirety and for all purposes.

FIELD

This disclosure relates to electronic systems and computer-implemented methods for selecting optical elements for vision correction or treatment.

BACKGROUND

Optical elements such as lenses in spectacles or eyeglasses, contact lenses, and intra-ocular lenses are commonly used for vision correction and eye growth control purposes. These optical elements correct for or introduce aberrations in the eye to enhance the vision of the user in some way. However, the eye is a complex organ, and selecting optical elements for the desired goal optimal vision correction may be difficult. Moreover, the outcomes and vision corrections produced by the same optical elements in different users may vary due to individual eye aberrations, biological/physiological processes, personal preferences, etc. Such variations in outcome and performance may be seen, for example, with presbyopic corrections used to aid the failing ocular accommodation system of aging eyes, or with the complicated interaction between the optical elements' design and aberrations of the eye when the eye moves or focuses and when the elements move relative to the eye's pupil, natural decentration, or in other scenarios.

There remains a continuing need for technology to enhance the optimal selection of optical elements. In particular, there is a need for technology that facilitates the selection of optical elements to optimize treatment, including vision correction, of individual users' eyes.

SUMMARY

Embodiments disclosed herein include computer-implemented tools to assist a clinician in selecting an optical element for treatment, such as correction, that provides optimal vision treatment or correction based on both the optical properties of the patient's eye and certain patient-specific use-case information such as viewing behavior, viewing preferences or to effect treatment such as to control myopia progression. Clinicians, eye care professionals and others can better accomplish patient-optimized optical element fitting or design by use of the tools.

A first example is a method for selecting a treatment or corrective optical element for a patient. The method may comprise receiving eye optical property information representative of optical properties of the patient's eye; accessing an optical element information source based upon the eye optical property information, wherein the optical element information source includes optical property information characterizing optical properties of each of a plurality of corrective optical elements; determining a set of one or more corrective optical elements from the optical element information source having optical property information within a range of the patient's eye optical property information; receiving use case information representative of patient-specific viewing characteristics of the user; determining use case optical property information based upon the use case information; determining a subset of one or more of the optical elements of the set of optical elements based upon the use case information; and determining a quality metric for each optical element of the subset based upon the eye optical property information and the optical property information of the optical element. Embodiments may also include generating an optical element score for each optical element of the subset based upon the quality metric of the optical element.

In some embodiments of the method, receiving use case information comprises receiving information representative of viewing behavior such as one or more of viewing distance, ambient light level or viewing time. In some embodiments, receiving use case information comprises receiving information representative of a desired optical outcome such as one or more of an astigmatism or a vision deterioration control correction.

In any or all of the above embodiments, determining use case optical property information comprises determining an addition to the eye optical property information. In any or all of the above embodiments, determining use case optical property information comprises determining a dose correction to the eye optical property information.

In any or all of the above embodiments, determining a quality metric comprises performing a virtual refraction. Generating an optical element score may comprise performing statistical analysis of the quality metric.

In any or all of the above embodiments, the method may include generating a ranking of the optical elements of the subset based upon the quality metrics.

A second example is a computer system for performing any or all embodiments of the methods of the first example described above.

A third example is a method for selecting a treatment or corrective optical element for a patient. The method may comprise: receiving eye optical property information representative of optical properties of the patient's eye; receiving use case information representative of patient-specific viewing characteristics of the user; determining use case optical property information based upon the use case information; accessing an optical element information source based upon the eye optical property information and the use case optical property information, wherein the optical element information source includes optical property information characterizing optical properties of each of a plurality of corrective optical elements; determining a set of one or more corrective optical elements from the optical element information source having optical property information within a range of the patient's eye optical property information and the use case optical property information; and determining a quality metric for each optical element of the set based upon the eye optical property information and the optical property information of the optical element. Embodiments may also include generating an optical element score for each optical element of the subset based upon the quality metric of the optical element.

In some embodiments of the method of the third example, receiving use case information comprises receiving information representative of viewing behavior such as one or more of viewing distance, ambient light level or viewing time. In some embodiments, receiving use case information comprises receiving information representative of a desired optical outcome such as one or more of an astigmatism correction or a vision deterioration control correction.

In any or all embodiments of the third example, determining use case optical property information comprises determining an addition to the eye optical property information. In any or all of the above embodiments, determining use case optical property information comprises determining a dose correction to the eye optical property information.

In any or all embodiments of the third example, determining a quality metric comprises performing a virtual refraction.

In any or all embodiments of the third example, generating an optical element score comprises performing statistical analysis of the quality metric.

In any or all embodiments of the third example, the method may further comprise generating a ranking the optical elements of the subset based upon the quality metrics.

A fourth example is a computer system for performing the method of any and all embodiments of the third example described above.

DETAILED DESCRIPTION

Figure 1:
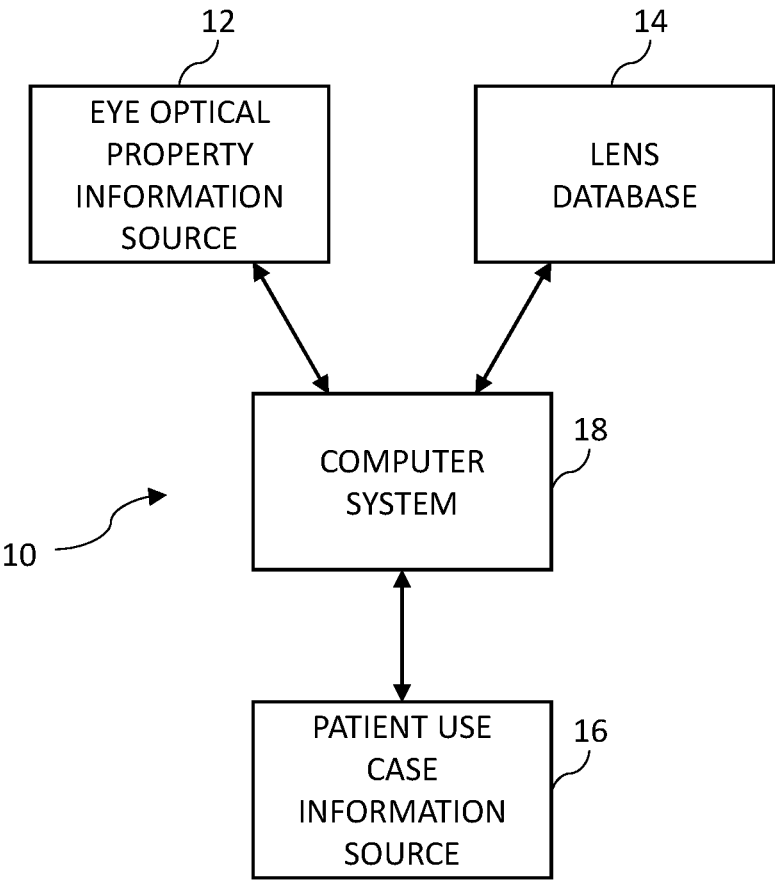
FIG. 1 is a diagrammatic illustration of a system that can operate to select user-optimized vision correction lenses in accordance with embodiments.

FIG. 1 is a diagrammatic illustration of a system 10 in accordance with embodiments. The system 10 can operate and be used by clinicians such as ophthalmologists or optometrists, vision correction element manufacturers or other system operators or eye care professionals, to select optical elements such as lenses having properties that will optimize vision correction or provide optical treatment properties for individual users such as patients. As shown, the system 10 includes an eye optical property information source 12, lens database 14 and patient use case information source 16 coupled to a computer system 18. Briefly, the eye optical property information source 12 may be an instrument, such as an aberrometer, that provides optical property information of an eye of the patient. Lens database 14 includes information on a plurality of lenses that may be available to the clinician, and associated optical property information for each of the lenses. Patient use case information sources 16 receive or generate information specific to the patient that define viewing behaviors of the patient, or that the clinician (e.g., eye care professional) may desire to be addressed by corrective or therapeutic lenses. Computer system 18 receives the patient's eye optical property information from source 12 and use case information from use case information sources 16, and processes that information along with the optical property information of the lenses in lens database 14, to identify and provide sets of one or more of the lenses from the lens database that may optimize treatment for the eye of the patient. In particular, the system 10 may identify in the database 14 lenses or other corrective optical elements that optimize treatment for each of one or both eyes of the patient based on their eye optical property information and their viewing behaviors represented by the use case information. In embodiments, for example, the computer system 18 provides sets of one or more lenses or other corrective optical elements from the database 14 that may optimize vision correction for the patient.

For example, system 10 may identify lenses that account for both optimal clinical prescription refractive values such as sphere (SPH), cylinder (CYL) and/or axis (AXS) (e.g., defining overall strength of correction and/or amounts and directions of astigmatism), and other patient-specific characteristics. Patient-specific characteristics that may be accommodated include, for example, vision optimization for distance viewing (e.g., sports vision performance), presbyopia (e.g., age-related difficulty seeing close objects) including monovision (e.g., one eye corrected for near viewing and the other for far viewing), myopia (nearsightedness) progression control (e.g., in a child or young adult), viewing distances (e.g., whether the patient prefers to maximize visual acuity for objects at relatively close or relatively far distances) and/or viewing light levels (e.g., whether the patient prefers to maximize visual acuity of viewing in relatively bright or relatively dark settings), eye pupil size associated with light level and viewing distance, the eye's focusing ability, amblyopia (e.g., in a child with vision development asymmetries between both eyes).

Eye optical property information sources such as 12 are generally known and commercially available. Instruments such as aberrometers, for example, provide wavefront (i.e., slope, error vergence, etc.) information defining the optical properties of the patient's eyes for every point on the pupil. Main or principle optical qualities of the patient's eyes provided by an aberrometer may, for example include a wavefront error Weye and an amplitude function Aeye. Weye, which may be specified in terms of parameters such as polar coordinates r (radial distance), e (angle) or Cartesian coordinates x,y that define a matrix of light ray deviations for a set of points in the pupil for a corresponding set of ray incidence angles. Weye may be measured in "one shot" corresponding to a single target (e.g., eye chart), or by a "sweep" (e.g., viewing distances and/or viewing angels) corresponding to multiple targets. Weye may include information about a light ray journey towards the retina, sufficient to obtain wavefront-derived optical qualities. Aeye may also be specified in terms of coordinates such as r, O and d, and defines a matrix of light ray transmission/attenuation for the set of points in the pupil. Aeye may include information about light ray transmission in the pupil plane including pupil shape, pupil apodization (e.g., modeling diminishing light ray efficiency towards the edges) and attenuation due to cataracts, other irregularities, etc.

The optical information provided by optical property information source 12 such as an aberrometer may also be used (e.g., by the computer system 18) to determine certain secondary optical qualities of the patient's eyes, such as one or more qualities defined in a pupil plane (PP) and/or an image plane (IP). Pupil plane qualities can include a set of values corresponding to clinical prescription refractive values, ray vergence (e.g., sagittal optical power), ray curvature, with can also be represented as profiles (cross sections), or histograms. In embodiments, the refractive scalar values may be defined in power vector form with M (sphere equivalent) and J0, J45 (horizontal and oblique astigmatism). These pupil plane values may, for example, be calculated (e.g., by the computer system 18) directly from the wavefront error Weye or indirectly from image quality metrics. Image plane values may include one or more of image quality (IQ) metrics, through-focus or virtual defocus curves, point-spread functions (PSF) optical transfer functions (OTF, e.g., comprising the magnitude transfer function (MTF) or phase transfer function (PTF)) and retinal qualities. Examples of image quality metrics include VSX (visual Strehl ratio), VSOTF (Strehl ratio based on OTF), AREAMTF (area computed in the frequency domain by the MTF method) or LIB (light-in-the-bucket). Retinal qualities can include the neural weighing function (NWF), contrast sensitivity function (CSF), or spectral sensitivity function. Furthermore, spectral interactions of light with ocular surfaces such as longitudinal or transverse chromatic aberration (LCA, TCA, respectively) may be based upon a standard observer or individually measured in the patient. Other embodiments may use other instruments or approaches for providing the eye optical property information, such as by clinical testing, optical theory, or autorefraction among others.

Figure 2:
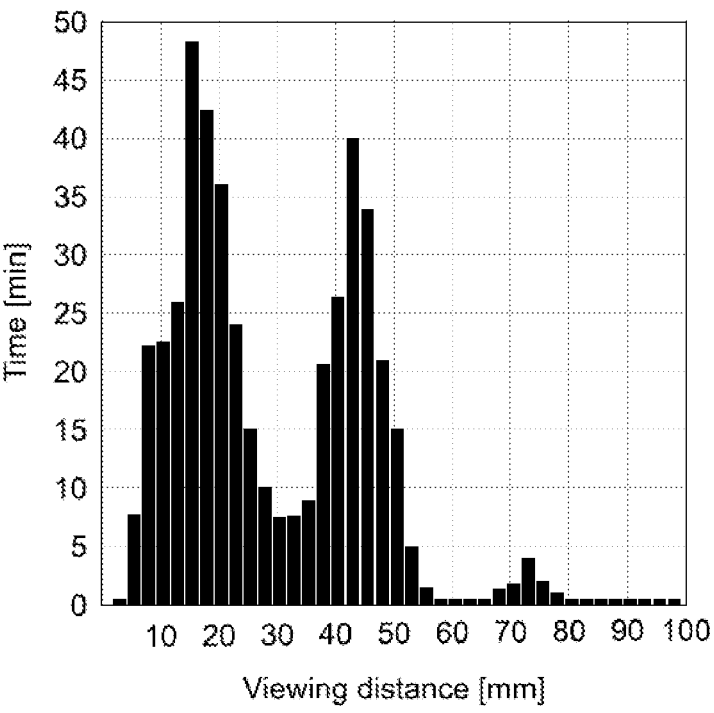
FIG. 2 is a graphical illustration of an exemplary distribution of viewing times at different viewing distances for a patient that may be provided, for example, by the patient use case information source shown in FIG. 1, in accordance with embodiments.

Examples of patient use case information sources 16 include electronic devices (e.g., mobile devices such as smartphones and tablets) used and viewed by the patient, information collected from the patient (e.g., through questionnaires and converted to electronic form), and/or information collected from a clinician (e.g., in the course of treating the patient and converted to electronic form). Use case information sources 16 may also include devices on a computer system regularly used by the patient (e.g., a work computer). For example, face-distance or viewing distance profiles (Dvb) and/or viewing time (Tvb) (e.g., screen time) may be determined from mobile devices or sensors on the computer system used by the patient. FIG. 2 is a graphical illustration of an exemplary multi-day (e.g., ten day) distribution of viewing times at different viewing distances for a patient. Information such as distance (e.g., mm), target vergence (TV) (e.g., in D (diopters)) and refractive state (RS) may be determined from information of these types. Statistics such as diopter-hours (Dhr) or average Dhr may be determined for a desired range of different time periods (e.g., daily, weekly or monthly). Estimates of surround distances of the visual field may be based on the target vergence obtained by these approaches.

Figure 3:
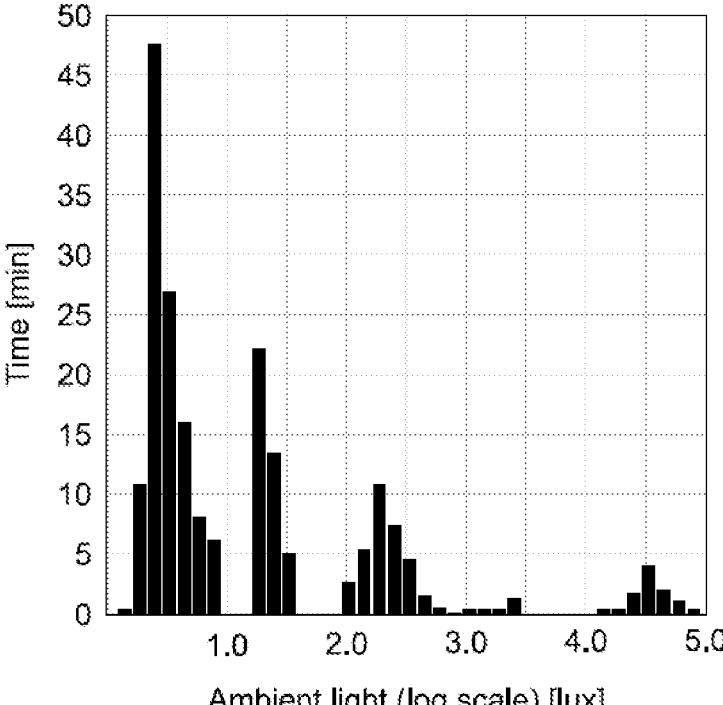
FIG. 3 is a graphical illustration of an exemplary distribution of viewing times at different ambient light levels for a patient that may be provided, for example, by the patient use case information source shown in FIG. 1, in accordance with embodiments.

Ambient light levels (Lvb) may be determined from mobile and other devices used by the patient. FIG. 3 is a graphical illustration of an exemplary multi-day (e.g., ten day) distribution of viewing times at different ambient light levels (e.g., luminance flux levels (lux)) for a patient. Statistics such as lux-hours (lux hr) or average lux hr may be determined for a desired range of different time periods. By way of example, the Zakharov U.S. Pat. No. 11,058,294 and the Zakharov U.S. Patent Application Publication 2021/0247626 describe devices for collecting viewing behavior information of users, and are incorporated herein by reference in their entireties and for all purposes. Other devices and/or approaches may be used to obtain viewing behavior information elements of these or other types in other embodiments. For example, a camera on the back of a device being viewed by the patient (or, e.g., a range finder or time of flight sensor) can collect an image that may be processed (optionally by artificial intelligence (AI) approaches) to measure both distances of the device to the patient's face and distances in the surrounding visual field.

Figure 4A:
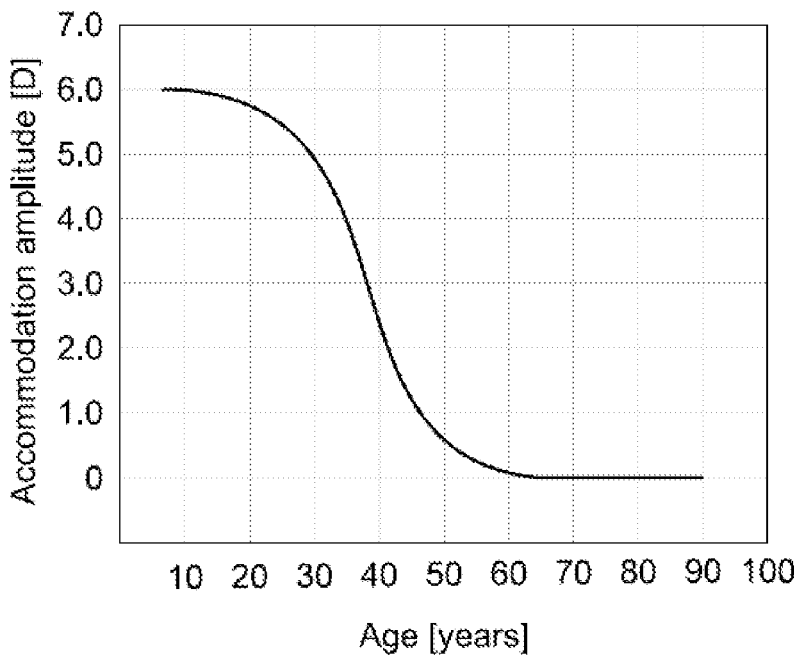
FIGS. 4A and 4B are graphical illustrations of exemplary graphs of amplitude of accommodation and gain, respectively, vs. age, representative of information provided by the patient use case information source shown in FIG. 1, in accordance with embodiments.
Figure 4B:
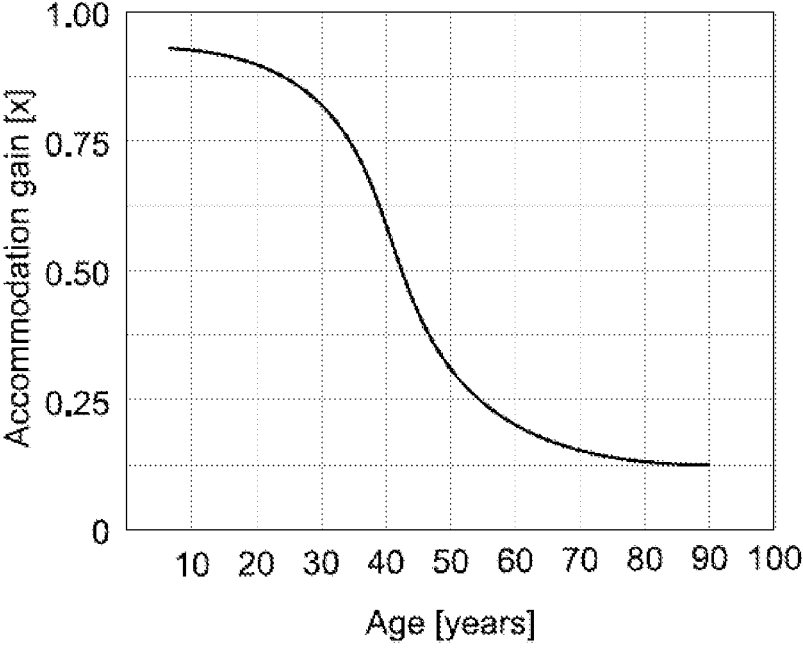
Figure 5:
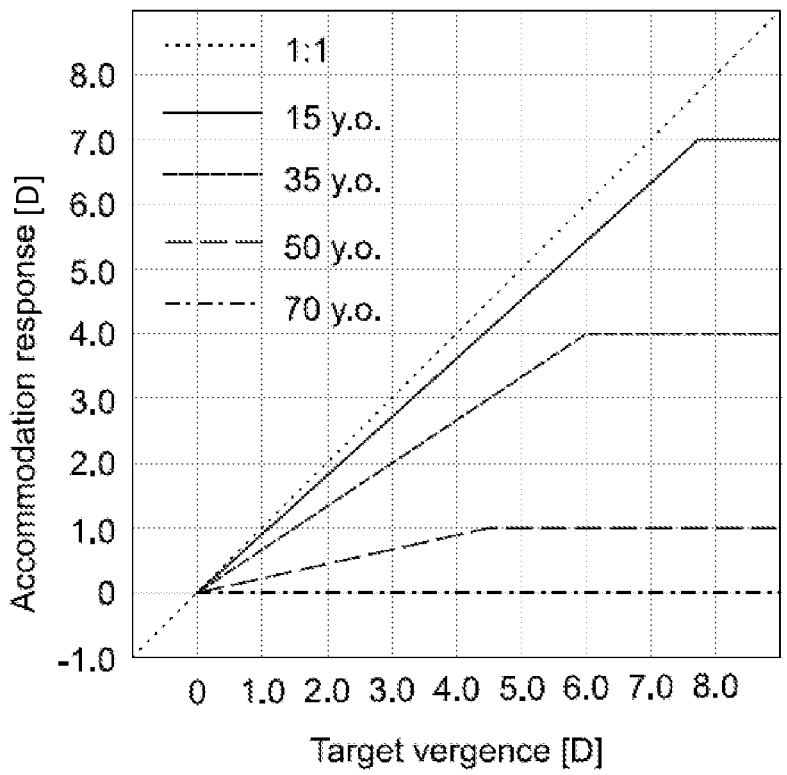
FIG. 5 is a graphical illustration of an exemplary graph of accommodative response vs. target vergence, representative of information provided by the patient use case information source shown in FIG. 1, in accordance with embodiments.
Figure 6:
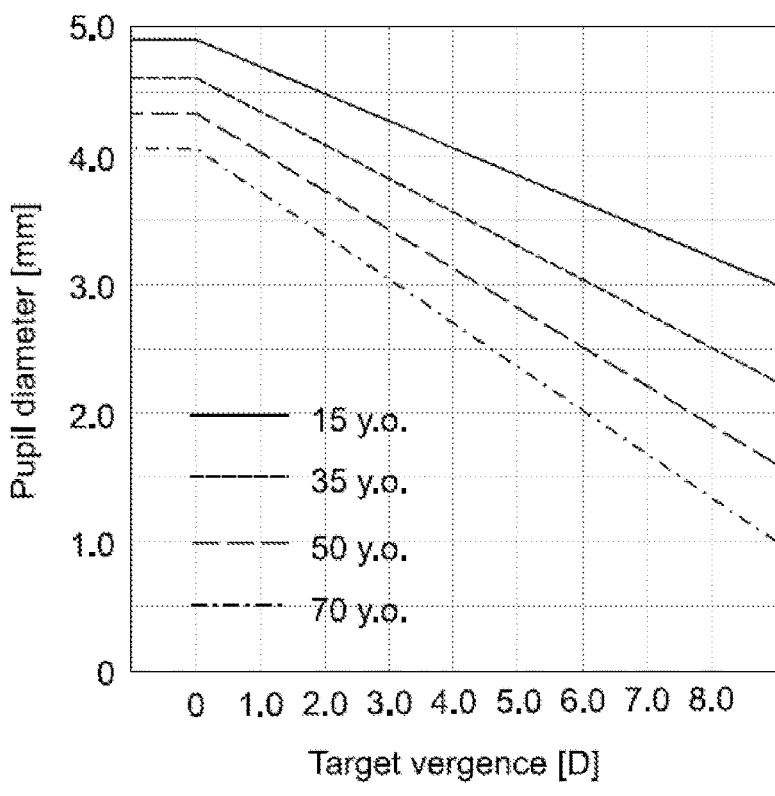
FIG. 6 is a graphical illustration of an exemplary graph of pupil diameter vs. target vergence, representative of information provided by the patient use case information source shown in FIG. 1, in accordance with embodiments.
Figure 7:
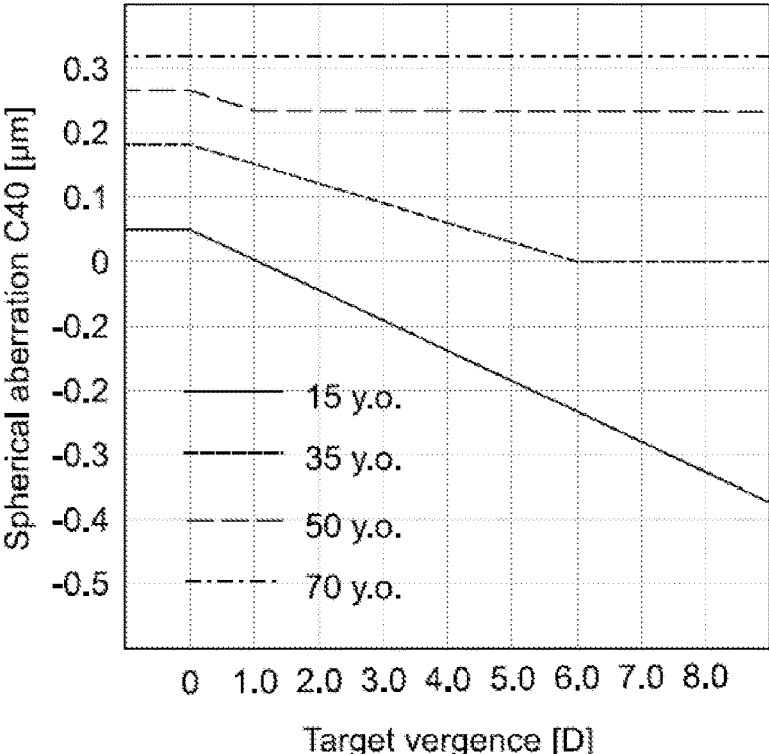
FIG. 7 is a graphical illustration of an exemplary graph of spherical aberration vs. target vergence, representative of information provided by the patient use case information source shown in FIG. 1, in accordance with embodiments.

Use case information in the form of preference information may include, for example, one or more of amplitude of accommodation (AA), accommodative gain (AG), accommodative response (AR), pupil diameter (r) or spherical aberration (SA). For example, amplitude of accommodation (e.g., specified in diopters) and/or accommodative gain (e.g., specified as a coefficient from zero to one) may be determined based upon age. Accommodative response and/or pupil diameter may be determined based upon target vergence and/or age and specified in diopters or mm. Spherical aberration may be determined based upon target vergence and/or accommodative response and specified in diopters. FIGS. 4A and 4B are graphical illustrations of exemplary graphs of amplitude of accommodation and gain vs. age, respectively. FIG. 5 is a graphical illustration of an exemplary graph of accommodative response vs. target vergence (including for example accommodative gain and amplitude from age). FIG. 6 is a graphical illustration of an exemplary graph of pupil diameter vs. target vergence (age-parameter). FIG. 7 is a graphical illustration of an exemplary graph of spherical aberration vs. target vergence (age-parameter).

Preference information of these and other types may be modeled, approximated, measured experimentally, or obtained from the patients or their clinicians. Patients may provide preference information describing their vision preferences, objectives and/or history. For example, one working age patient may want their vison correction optimized for night driving, which may occur in relatively larger pupil and relatively low light conditions. Another relatively older patient may want their vison correction optimized for daylight reading, which may occur in relatively smaller pupil and higher light conditions. Yet another relatively older patient may prefer a progressive optical design lens where the near-viewing add is modulated with downward gaze, whereas another patient of a similar age may prefer a monovision lens treatment where one eye is corrected for near and the other for far viewing, providing both types of vision simultaneously. A clinician may want to provide a prescription for a child patient that is optimized to control the progression of myopia, or may want to address asymmetries in the vision development process in both eyes for a child with amblyopia.

Lens database 14 stores information identifying a plurality of different lenses or other corrective optical elements and optical property information associated with each of the lenses. For example, lens database 14 may store information on lenses of different types, including one or more of contact lenses, intra-ocular lenses and/or spectacle (e.g., eyeglass) lenses. Alternatively or in addition, the lens database 14 may include information on lens designs and/or geometries. For each of the different types of lenses, the lens data base 14 stores information on a plurality of lenses of the type, where each of the plurality of lenses has different properties, such as for example different optical properties. For example, lens database 14 may include lens information for a plurality of contact lenses, a plurality of intra-ocular lenses and/or a plurality of spectacle lenses, where each of the lenses has different optical properties associated with (1) a range of refractive corrections (e.g., a range of different positive and negative SPH values) to accommodate different amounts of farsightedness and nearsightedness), and/or (2) a range of different astigmatism corrections (e.g., a range of different CYL and AXS values) to accommodate different amounts and types of astigmatisms. In embodiments, the optical properties of the lenses in the lens database 14 may be defined in terms of the clinical prescription refractive values SPH, CYL and AXS. Alternatively or in addition, the optical properties of the lenses in the lens database 14 may be defined in terms of other values, such as for example by power vector values or wavefront error, among others.

Figure 8:
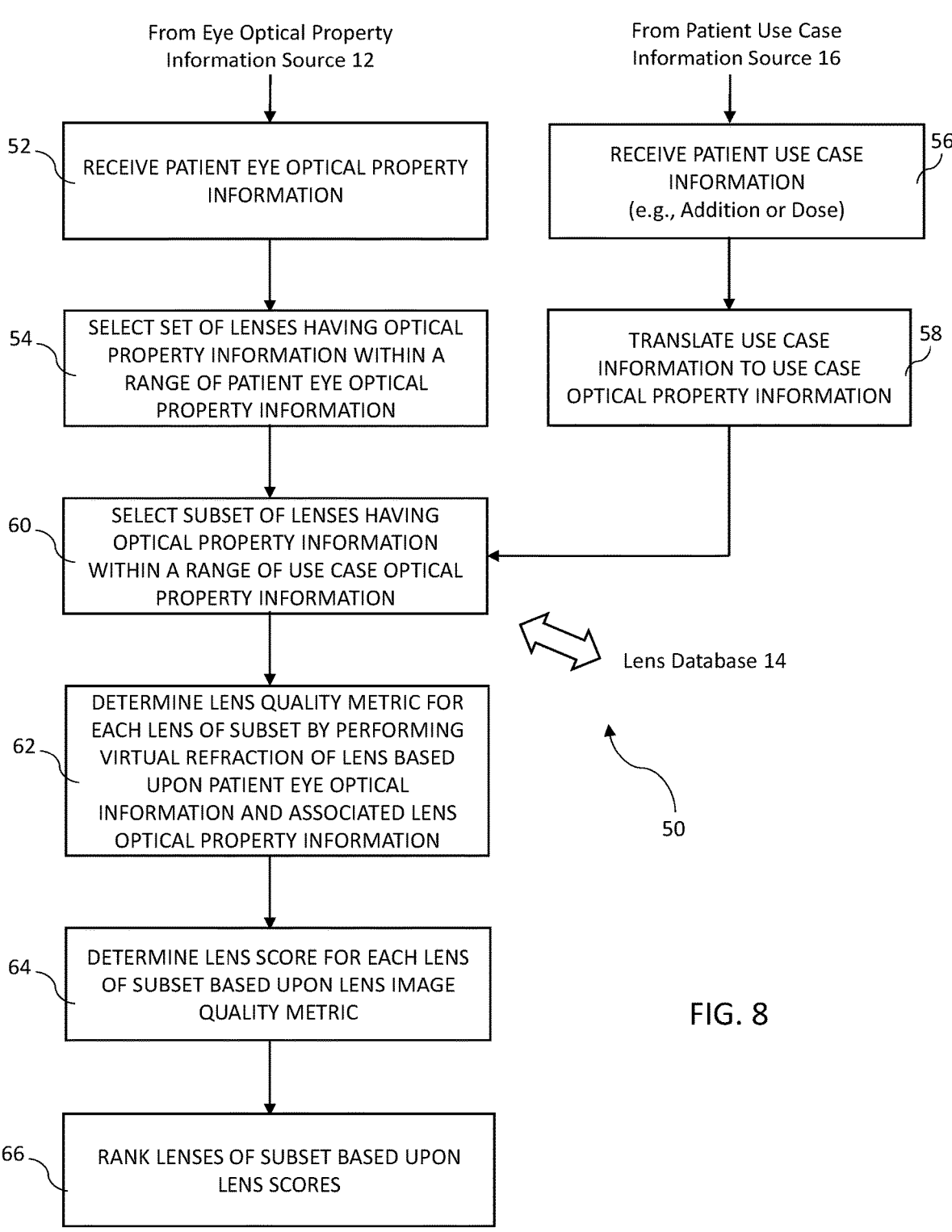
FIG. 8 is a block diagram of a method in accordance with embodiments that can be performed by the system shown in FIG. 1.

FIG. 8 is a diagrammatic illustration of a method 50 that can be performed by the computer system 18 of the system 10 shown in FIG. 1. Although the method 50 is described in connection with the selection of lenses for one eye of a patient, the method can be used to select lenses for each of one or both eyes of the patient. As shown by step 52, optical property information of the patient's eye is received from the aberrometer 12. The computer system 18 then selects from the lens database 14 a set of one or more lenses within a range of the patent eye optical property information as shown at step 54. The lenses selected at step 54 may be limited to particular types of lenses suitable for the patient, for example contact lenses, spectacle lenses or intra-ocular lenses. The lenses are selected at step 54 based upon the patient eye optical property information received and step 52, and the lens optical property information associated with the lenses in the lens database 14. The lenses of the selected set will have optical properties that may be suitable for correcting the vision in the eye of the patient.

The lenses of the set may be selected to provide vision correction within a range, such as for example a predetermined range, of the patient eye optical property information. For example, in embodiments where the patient eye optical property information is representative of SPH, CYL and AXS values, a set of lenses having SPH, CYL and AXS values within a predetermined range of those of the patient eye optical property information may be selected at step 54. In effect, at step 54 the method 50 filters out lenses in the database 14 that are likely not suitable for correction of the patient's vision. For example, lenses having negative SPH values will not be selected for patients requiring corrective lens with positive SPH values. Lenses having positive SPH values beyond a certain range of the patient's SPH value, such as for example two diopters, may also be not selected. Similarly, if the patient's eye optical property information indicates no astigmatism, at step 54 lenses in the database 14 having CYL and AXS values for astigmatism correction may not be selected.

An advantage of step 54 is that it may reduce the time and/or computing resources needed to perform certain other steps of the method 50 such as steps 62, 64 or 66 described below. However, other embodiments of method 50 may omit step 54. For example, if the time or computing resources for the method 50 are not a limiting factor, steps such as 62, 64 or 66 may be performed for all of the lenses in the lens database 14. Similarly, depending upon the amount of conservation of time or computing resources is desired, relatively larger or smaller sets of lenses may be selected at step 54, for example by the clinician varying the range between the patient eye optical property information and the lens optical property information defining the selected lenses.

At step 56, the use case information is received from the patient use case information source 16. The use case information is translated to patient-specific use case optical property information at step 58, and facilitates the use of a dynamic eye model in connection with the determination of optimal, patient-specific lens selection.

In embodiments, the use case optical property information generated at step 58 may be defined or specified in terms of the optical property information defining the optical property information of the lenses selected at step 54 (e.g., scalar values such as SPH, CYL and AXS values). In embodiments, at step 58 the method 50 determines the use case optical property information in terms of one or both of an addition or a dose. In general, an addition may be a change to an optical property of a lens that is primarily intended to enhance a near viewing feature of the patient's vision, such as for example to facilitate reading in presbyopic patients. A dose may also be a change to an optical property of a lens (such as optical power or contrast) that is primarily intended to attain a treatment effect over the patient's vision, such as limiting the rate of axial eye growth known to cause myopia (nearsightedness). Both the addition and the dose may be determined based upon one or more use case information elements, such as Dvb, Lvb or Tvb described above. As described in greater detail below, the use case optical property information is used to filter or fine-tune the selection of lenses for the patient to identify lenses that optimize the vision correction for the particular viewing behavior or other desired use case of the patient.

Figure 9A:
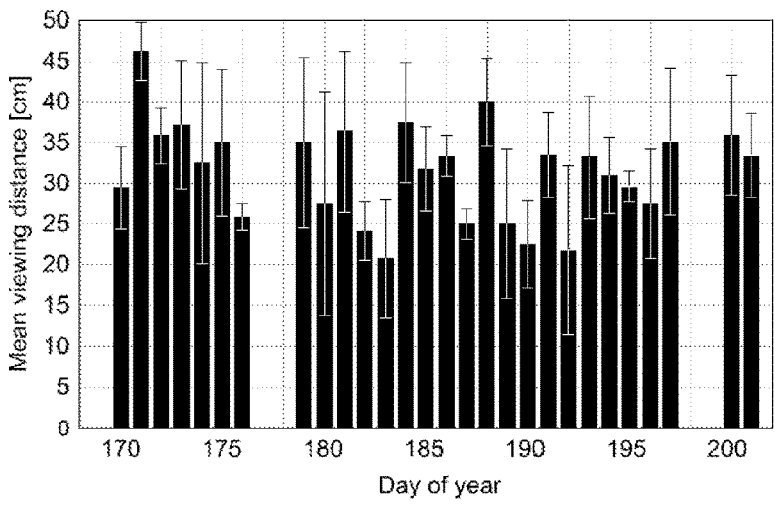
FIGS. 9A-9C are graphical illustrations of exemplary viewing behavior information in the form of face-device distance, ambient light level of viewing and screen time, respectively, for a patient that may be provided, for example, by the patient use case information source shown in FIG. 1, in accordance with embodiments.
Figure 9B:
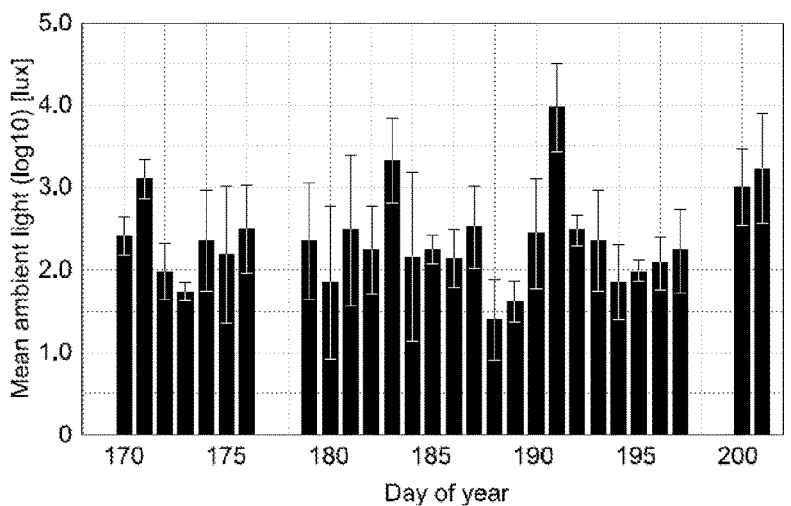
Figure 9C:
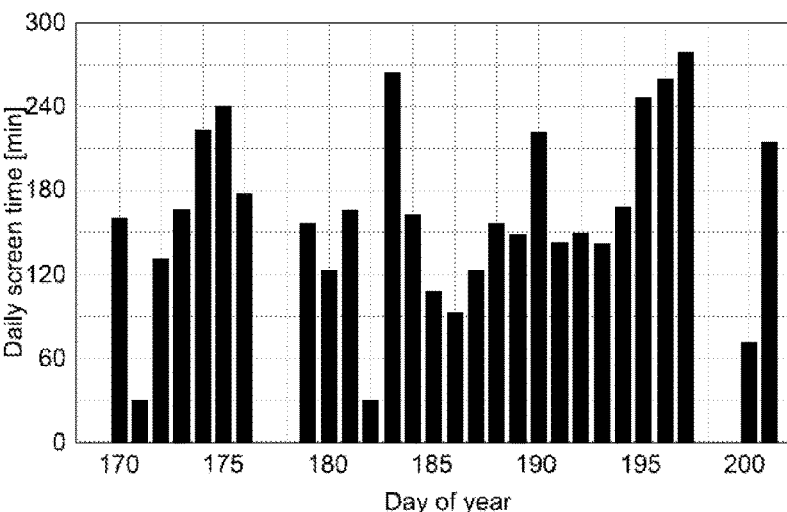

In connection with several examples of step 58, FIGS. 9A, 9B and 9C illustrate exemplary viewing behavior information in the form of face-device distance, ambient light level of viewing and screen time, respectively, obtained from by a mobile device of a patient over multi-day (e.g., sixty-four day) periods. At step 58 the computer system 18 may calculate information elements such as Dvb, Lvb and/or Tvb from the data shown in FIGS. 9A-9C.

One example of step 58 may relate to a presbyopic eye (e.g., age-related difficulty reading or otherwise seeing near objects) of a patient having viewing behaviors characterized by the Dvb, Lvb and/or Tvb described above in connection with FIGS. 9A-9C. Based on one or more of the Dvb, Lvb and/or Tvb, an addition can be determined at step 58 to provide an optimal and personalized amount (e.g., in a spectacle lens or contact lens) to enhance the patient's ability to see near objects. In embodiments, the addition may be a set of scalar values (e.g., a gradient of addition values in diopters describing a spectacle lens area with progressive addition).

In connection with this example, the term "over correction" may refer to obtaining the difference between a patient's current prescription and their actual refraction. In presbyopia, this may be related to observations that past forty or so years of age, the patients' near point (NP), which marks the near end of their interval of clear vision drifts further away over time (or the process may continue throughout life, but becomes problematic at that age). This drift may be accommodated by or require updating the prescription to increase the addition of the reading glasses or add in multi-focal lens or power in mono-vision prescriptions.

Viewing behavior information from a patient device while the patient is wearing their current prescription may be received. Such viewing behavior information may, for example, include one or more of (1) distribution of viewing distances expressed in diopters per a period (e.g., week) (VD=f(t)), (2) any other measure of near viewing behavior, which may include near work distance, time and task, and/or (3) obtain pupil size and illumination information aligned to different viewing distances and tasks.

Preference information may be received, for example via a patient interview or questionnaire. Such preference information may, for example, include one or more of (1) a preference for optical correction type (e.g., contact lenses CL, progressive spectacle lenses SL or mono-vision) which may be the patient's personal preference, and based on lifestyle conditions (e.g., athletics), (2) a preference for viewing conditions (e.g., patients may express a preference for optical corrections optimized for night driving, sports, reducing digital eye fatigue, etc.) and/or (3) a measurement or otherwise obtained preference for both sighting and sensory eye dominance, and some measure of tolerability to monocular blur.

The patient's current prescription CP may also be obtained.

An ordered list of optical correction types may be obtained from, for example, one or more of (1) preference information, and/or (2) a computer-implemented algorithm for obtaining optical correction types. Such a computer-implemented algorithm may include, for example, steps such as (1) if the distribution of viewing distances expressed in diopters indicated that the mean of minimum viewing distances over different time periods or different samples is greater than a typical comfortable viewing distance (e.g., 33 cm), and (2) if the patient is already wearing spectacle lenses for distance correction, then (3) select progressive spectacle lenses with presbyopic add as a first-order optical correction.

Near-viewing addition or range may for example, be obtained from one or more of (1) preference information, (2) a computer-implemented algorithm for obtaining near-viewing addition (in diopters) from viewing information and the current prescription (e.g., Add=f(VD, CP), and/or (3) applying a computer-implemented weighing algorithm to obtain the near-viewing addition from (1) and (2).

Another example of step 58 relates to a myopic eye (e.g., nearsightedness with difficulty seeing distant objects) of a patient having viewing behaviors characterized by the Dvb, Lvb and/or Tvb described above in connection with FIGS. 9A-9C. Based on one or more of the Dvb, Lvb and/or Tvb, a dose can be determined at step 58 to provide an optimal control dose to a lens to minimize the progression of myopia in the patient and thereby optimize the health of their eye. In embodiments, the dose may be a set of scalar values (e.g., in diopters).

Embodiments of step 58 may make use of known eye optical property and/or treatment information. In connection with this example, certain research has demonstrated that for each additional ten hours of reading for pleasure per week and at the end of a progression interval, there was an associated increase in average annual (myopia) progression by −0.08 D. Also, certain research has shown that diopter hours for subjects was significantly higher on weekdays compared to weekends.

Viewing behavior information may be received from a patient device. Such information may, for example, be one or more of (1) the number of diopter hours (dh) per a period (e.g., a week), (2) mean daily diopter hours for a period (e.g., a week), (3) a more comprehensive characterization of the distribution of near work distance over time, and/or (4) any other measure of near work which may include near work distance over time.

Preference information may be received, for example via a patient interview or questionnaire, or other source such as a clinician. Such preference information may, for example, include one or more of (1) preference for optical correction type (e.g., contact lenses CL, spectacle lenses SL, orthokeratology (OrthoK)) (for example, parents of a young child may show a preference for spectacle lenses), and/or (2) preference for myopia control dose amount (in diopters) (for example optical preference information can include a history of accelerating myopia progression, which can show a need to increase or introduce a myopia control dose, which may also be obtained from a clinician).

An ordered list of optical correction types may be obtained from, for example, one or more of (1) preference information, (2) a computer-implemented algorithm to obtaining optical correction types, and/or (3) applying a computer-implemented weighing algorithm to obtain an ordered list of optical correction types from (1) and (2). An example of a computer-implemented algorithm for obtaining optical correction types may include (1) if dh is less than a predetermined value a high myopia control dose may be used due to a high amount of near work, (2) if the patient (e.g., a child) is old enough (e.g., greater than ten years of age) to wear contact lenses, (3) select contact lenses as a first order optical correction type because contact lenses are worn every day as opposed to spectacle lenses with can be removed and diminish treatment effectiveness. An example of a computer-implemented weighing algorithm may include (1) if the patient is no longer a child (e.g., is greater than twenty-five years of age), and (2) presents a history of myopia no greater than a predetermined amount such as −6.0 D, (3) viewing information shown e.g., by diopter hours is greater than a predetermined amount (e.g. representative of a heavy smartphone user, (4) the patient has been a spectacle lens wearer since a young age and wants to try something different, (5) select OrthoK as a first-order optical correction type because it is worn at night and removed during the day, offering good vision and low eye fatigue due to screens.

The myopia control dose amount or range may be obtained, for example, from one or more of (1) the preference information, (2) a computer-implemented algorithm for obtaining myopia control dose (in diopters) from viewing information, and/or (3) applying a computer-implemented weighing algorithm to obtain the myopia control dose from (1) and (2). Examples of computer-implemented algorithms for obtaining the myopia control dose include one or more of (1) D=f (diopter hours per period), (2) D=f (mean daily diopter hours per period, and/or (3) D–f (distance, time per period), etc.

Yet another example of step 58 relates to accommodative esotropia, a type of strabismus, or eye misalignment. This condition is also sometimes known as refractive esotropia and is a relatively common form of esotropia (crossed eye) in children. This condition may occur in children who are typically more farsighted (hyperopic) than usual. In general, the closer an object is to the eye, the greater the amount of accommodation that is required. A side effect of the accommodative effort can be excess convergence or crossing of the eyes.

The presence and magnitude of accommodative esotropia can be detected by monitoring binocular eye convergence as a function of accommodation (viewing distance). A first step to help treat accommodative esotropia may involve the prescription of eyeglasses or contact lenses to correct the patient's refractive error (hyperopia). This step can reduce the convergence or crossing stimulus and the eyes will straighten as they relax. Glasses or contacts which are used to treat accommodative esotropia are preferably worn full time.

Some patients/children may not need any correction to see better, but they may benefit from correction for their high hyperopia (far sightedness) to avoid over convergence and eye crossing at near.

Viewing behavior information may be received from a patient device. Such information related to accommodation may, for example, include one or more of (1) number of diopter hours (dh) per a period (e.g., week), (2) mean daily dh for a period (e.g., week), (3) a more comprehensive distribution of near work distance over time, and/or (4) any other measure of accommodative demand (A) which includes near work distance and time.

Viewing behavior information related to binocular convergence, for both eyes, the gaze direction, which can be obtained from the position of the pupil with respect to the contour of the eye, or with respect to another face landmark such as the tip of the nose, may for example include one or more of (1) horizontal and vertical gaze angle (ga), (2) horizontal and vertical displacement (gxy), and/or (3) over a period of interest (e.g., a week).

Preference information may be received, for example via a patient interview or questionnaire. Such preference information may, for example, include one or more of (1) a preference for optical correction type (e.g., contact lenses CL, spectacle lenses SL, orthokeratology OrthoK) (for example, parents of a young child may show a preference for spectacle lenses), (2) a preference for daily wearing time (for example, optical preference information can include a history of strabismus in the family which may indicate a longer daily wearing time).

An ordered list of optical correction types may be obtained from, for example, one or more of (1) the preference information, and/or (2) a computer-implemented algorithm for obtaining optical correction types. An example of a computer-implemented algorithm for obtaining optical correction types may include (1) if the amount of binocular convergence C=f(A) indicates excessive convergence which can include eyes crossing, (2) the child is a moderate or high hyperope (e.g., +3.0 D or greater), (3) the child is younger than a certain age (e.g., age less than ten), (4) select spectacle lenses (eyeglasses SL) as first-order optical correction type because spectacle lenses are more convenient for young children to wear over an extended period.

In some cases, children may develop excessive amounts of eye crossing (esotropia) at near, such as while reading. This may occur even when wearing the correct glasses to correct their farsightedness (hyperopia) and they may have perfectly straight eyes when looking at distant objects. These children may benefit from making the lower, reading portion of the eyeglasses "extra strong" with bifocals. In an example of this type, information that may be obtained can include one or more of (1) hyperopia correction amount (in diopters), and/or (2) minimum daily wearing time. The correction for accommodative esotropia may be obtained from one or more of (1) the preference information, (2) a computer-implemented algorithm for obtaining a hyperopia correction amount and daily wearing time (in diopters) from viewing information (e.g., D, t=f (C, A per period)), and/or (3) a computer-implemented weighing algorithm to obtain the hyperopia correction amount and daily wearing time from (1) and (2).

At step 60, a subset of the set of lenses determined at step 54 is selected based upon the use case optical property information determined as step 58. For example, following the addition determined for the presbyopic eye example described above in connection with step 58, lenses in the set determined at step 58 that do not accommodate presbyopic viewing enhancement may be excluded from the selected subset. Following the dose determined for the myopic eye example described above, lenses in the set that do not accommodate the myopic control dose (e.g., presbyopic lenses) may be excluded from the selected subset.

Figure 10A:
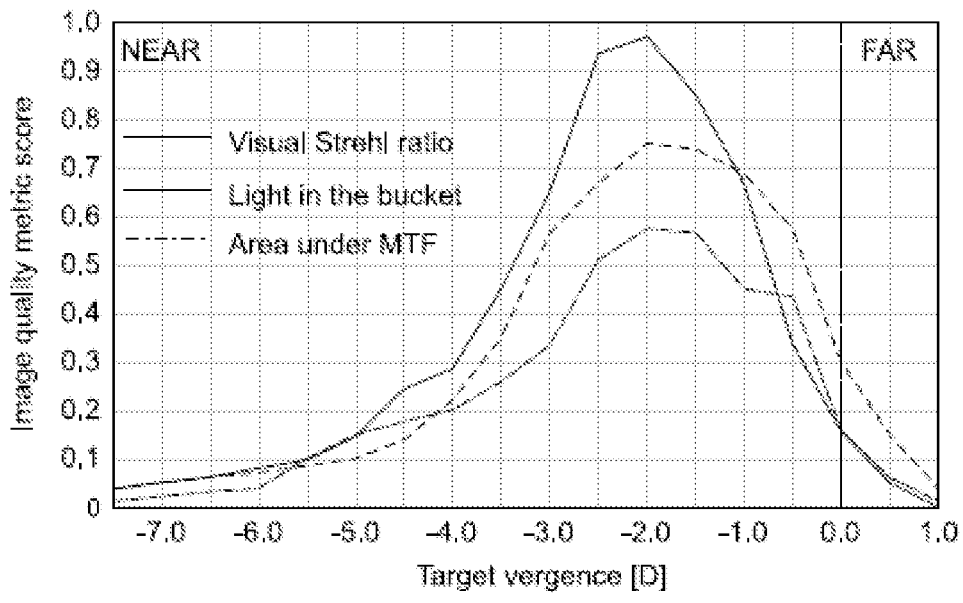
FIG. 10A is a graphical illustration of image quality analyses of a lens using three different image quality metrics (Visual Strehl ratio, Light in the bucket, and Area under MTF), in accordance with embodiments.
Figure 10B:
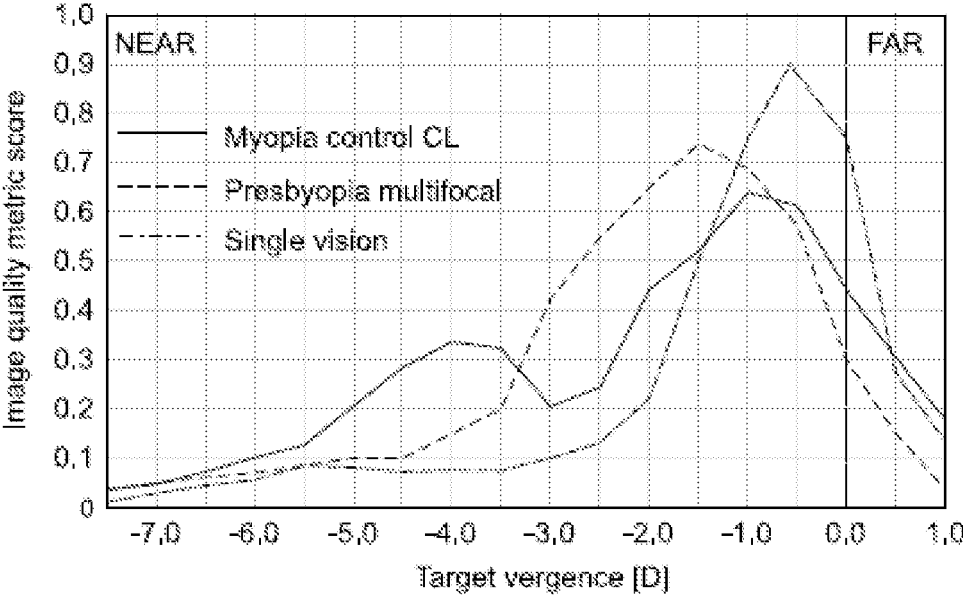
FIG. 10B is a graphical illustration of image quality analyses of three different lenses using an image quality metric, in accordance with embodiments.

At step 62 a lens quality metric is determined for each lens of the subset determined at step 60. The lens quality metric is information that may be used to determine whether and to what degree or extent the associated lens will enhance the vision of patient when the lens is used in connection with the eye of the patient. The lens quality metric may be determined by performing a virtual refraction of the lens based upon both the patient eye optical property information and the associated lens optical property information. In effect, the lenses of the subset are digitally "put on" the patient's eye to provide information representative of the quality of the image produced by the lens and eye combination. This can be achieved by means of superposition in the pupil plane of the eye and lens wavefronts corresponding to a viewing scenario (e.g., parameters such as pupil size (which may depend upon factors such as light level and viewing distance), accommodative gain and amplitude, and viewing distance) corresponding to the patient's use case. In embodiments, the image quality metric may be generated by performing virtual refractions of the lenses evaluated with image quality metrics such as VSX, Light in the bucket and AREAMTF approaches. As examples, FIG. 10A is a graphical illustration of image quality analyses of one lens using three different image quality metrics (Visual Strehl ratio, Light in the bucket, and Area under MTF). FIG. 10B is a graphical illustration of image quality analyses of three different lenses using one image quality metric.

At step 64 a lens score may be determined for each of the lenses of the subset determined at step 60 based upon the image quality metric. In embodiments, for example, the lens score may be determined by statistical analysis approaches, such as for example determining the mean or full width half maximum (FWHM) values of the image quality metric, or the area under the curve of the associated image quality metric. The lens scores, and optionally the associated image quality metrics, may be presented, for example in textual or other graphical form, by a user interface the computer system 18 (not separately shown in FIG. 1). A clinician may then use the lens scores and/or image quality metrics in connection with decisions on what lenses to recommend or prescribe for the patient.

In some embodiments the computer system 18 may rank the lenses of the subset based upon the lens scores as shown by step 66. For example, the ranking may be an order, such as a decreasing order, based upon the lens scores, with the lenses having the highest lens scores ranked highest and the lenses with the lowest lens scores ranked lowest. The ranking may, for example, be sequential. Such a ranking may be useful to the clinician in the course of determining which lenses to recommend or prescribe for the patient.

Figure 11:
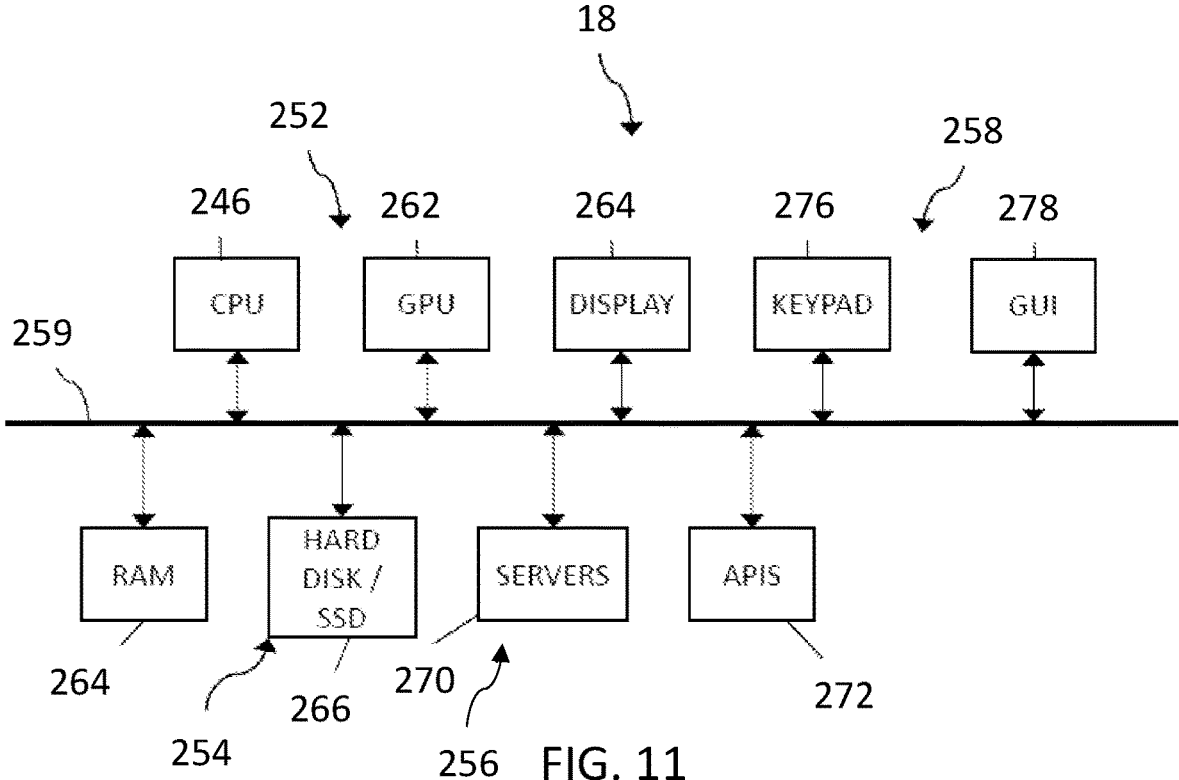
FIG. 11 is a diagrammatic illustration of components of an exemplary computer system, in accordance with embodiments

FIG. 11 is a diagrammatic illustration of an exemplary computer system 18. The illustrated embodiments of computer system 18 comprise processing components 252, storage components 254, network interface components 256 and user interface components 258 coupled by a system network or bus 259. Processing components 252 may, for example, include central processing unit (CPU) 260 and graphics processing unit (GPU) 262, and provide the processing functionality for the method 50. The storage components 254 may include RAM memory 264 and hard disk/SSD memory 266, and provide the storage functionality for the instructions defining the method 50 and/or the lens database 14. Operating system software used by the processing components 252 to implement methods described herein may be stored by the storage components 254. In embodiments, the network interface components may include one or more web servers 270 and one or more application programming interfaces (APIs) 272, for example to provide the interface functionality to functionality to aberrometer 12, lens database 14 and patient use case information source 16. Examples of user interface components 258 include display 274, keypad 276 and graphical user interface (GUI) 278, and may for example provide the functionality of the user interface displaying the image quality metrics, lens scores and/or rankings determined by method 50. Embodiments of computer system 238 may include other conventional or otherwise known components to implement the methods in accordance with embodiments described herein.

It is to be understood that the above description is intended to be illustrative, and not restrictive. Many other embodiments will be apparent to those of skill in the art upon reading and understanding the above description. For example, embodiments may not use the "two-step" approach described in connection with FIG. 8 (e.g., both the selection of the initial set of lenses at step 54 followed by the selection of the subset of lenses at step 60). In such alterative embodiments, the system may obtain a set of lenses having optical property information within a range of the patient eye optical property information and within a range of the use case optical property information (e.g., in "one step") based upon the eye optical property information and the use case optical property information. It is contemplated that features described in association with one embodiment are optionally employed in addition or as an alternative to features described in or associated with another embodiment. The scope of the invention should, therefore, be determined with reference to the appended claims, along with the full scope of equivalents to which such claims are entitled.

What is claimed is:

1. A method for selecting a treatment or corrective optical element for a patient, comprising:

receiving an eye optical property information representative of optical properties of the patient's eye;

selecting a set of one or more corrective optical elements from an optical element information source based upon the eye optical property information, wherein the selected set of corrective optical elements have optical property information within a range of the patient's eye optical property information, and wherein the optical element information source includes optical property information characterizing optical properties of each of a plurality of corrective optical elements;

receiving a use case information representative of patient-specific viewing characteristics of the user, wherein receiving the use case information comprises receiving information representative of viewing behavior such as one or more of a patient-specific viewing distance, a patient-specific ambient light level, or a patient-specific viewing time;

determining a use case optical property information based upon the use case information;

selecting a subset of one or more of the optical elements of the set of optical elements based upon the use case information;

determining a quality metric for each optical element of the subset based upon the eye optical property information and the optical property information of the optical element; and generating an optical element score for each optical element of the subset based upon the quality metric of the optical element.

2. The method of claim 1, wherein receiving the use case information comprises receiving information representative of a desired optical outcome such as one or more of an astigmatism correction or a vision deterioration control correction.

3. The method of claim 1, wherein determining the use case optical property information comprises determining an addition to the eye optical property information.

4. The method of claim 1, wherein determining the use case optical property information comprises determining a dose correction to the eye optical property information.

5. The method of claim 1, wherein determining the quality metric comprises performing a virtual refraction.

6. The method of claim 5, wherein generating an optical element score comprises performing statistical analysis of the quality metric.

7. The method of claim 1, further comprising generating a ranking the optical elements of the subset based upon the quality metric.

8. A computer system including one or more processors configured to perform the method of claim 1.

9. A method for selecting a treatment or corrective optical element for a patient, comprising:

receiving an eye optical property information representative of optical properties of the patient's eye;

receiving a use case information representative of patient-specific viewing characteristics of the user, wherein receiving the use case information comprises receiving information representative of viewing behavior such as one or more of a patient-specific viewing distance, a patient-specific ambient light level, or a patient-specific viewing time;

determining a use case optical property information based upon the use case information;

selecting a set of one or more corrective optical elements from an optical element information source based upon the eye optical property information, wherein the selected set of corrective optical elements have optical property information within a range of the patient's eye optical property information and the use case optical property information, and wherein the optical element information source includes optical property information characterizing optical properties of each of a plurality of corrective optical elements;

determining a quality metric for each optical element of the set based upon the eye optical property information and the optical property information of the optical element; and generating an optical element score for each optical element of the set based upon the quality metric of the optical element.

10. The method of claim 9, wherein receiving the use case information comprises receiving information representative of a desired optical outcome such as one or more of an astigmatism correction or a vision deterioration control correction.

11. The method of claim 9, wherein determining the use case optical property information comprises determining an addition to the eye optical property information.

12. The method of claim 9, wherein determining the use case optical property information comprises determining a dose correction to the eye optical property information.

13. The method of claim 9, wherein determining the quality metric comprises performing a virtual refraction.

14. The method of claim 13, wherein generating an optical element score comprises performing statistical analysis of the quality metric.

15. The method of claim 9, further comprising generating a ranking the optical elements of the set based upon the quality metric.

16. A computer system including one or more processors configured to perform the method of claim 9.

* * * * *